United States Patent
Weinstock et al.

(10) Patent No.: US 11,241,685 B2
(45) Date of Patent: Feb. 8, 2022

(54) SEPARATOR

(71) Applicant: SARSTEDT AKTIENGESELLSCHAFT & CO. KG, Nümbrecht (DE)

(72) Inventors: Mark Weinstock, Helmenzen (DE); Christian Wegener, Nümbrecht (DE); Ulrich Karrenberg, Marienheide (DE)

(73) Assignee: SARSTEDT AKTIENGESELLSCHAFT & CO. KG, Nümbrecht (DE)

( * ) Notice: Subject to any disclaimer, the term of this patent is extended or adjusted under 35 U.S.C. 154(b) by 214 days.

(21) Appl. No.: 16/608,776

(22) PCT Filed: Apr. 25, 2018

(86) PCT No.: PCT/EP2018/060602
§ 371 (c)(1),
(2) Date: Oct. 25, 2019

(87) PCT Pub. No.: WO2018/197565
PCT Pub. Date: Nov. 1, 2018

(65) Prior Publication Data
US 2020/0197929 A1    Jun. 25, 2020

(30) Foreign Application Priority Data
Apr. 26, 2017  (DE) ..................... 10 2017 108 937.3

(51) Int. Cl.
*B01L 3/00* (2006.01)
*A61B 5/15* (2006.01)
(Continued)

(52) U.S. Cl.
CPC ..... *B01L 3/50215* (2013.01); *A61B 5/150755* (2013.01); *B01D 21/262* (2013.01);
(Continued)

(58) Field of Classification Search
USPC .................. 422/533; 210/516, 513, 515, 518
See application file for complete search history.

(56) References Cited

U.S. PATENT DOCUMENTS 3,887,464 A    6/1975  Tyres
4,443,345 A    4/1984  Wells
(Continued)

FOREIGN PATENT DOCUMENTS

DE    60023823    8/2006
DE    69931584    5/2007
(Continued)

*Primary Examiner* — Nina Bhat
(74) *Attorney, Agent, or Firm* — Smartpat PLC

(57) ABSTRACT

A separator for separating a first from a second phase of a liquid in a tubular container includes a float made of elastic material having a circumferential sealing edge and at least one ballast fastened to the underside of the float. The density of the ballast is greater than the density of the float and the density of the entire separator lies in a value range between the density of the first phase and the density of the second phase of the liquid. In order to ensure an unrestricted light inflow of the liquid into volume regions of the container lying below the separator in the initial position, the float is designed disk-shaped; and that the ballast is designed in the form of a plurality of fingers extending away from the underside of the disk-shaped float, distributed at its edge.

12 Claims, 2 Drawing Sheets

(51) Int. Cl.
    *B01D 21/26*         (2006.01)
    *G01N 33/49*         (2006.01)
    *B01D 21/30*         (2006.01)

(52) U.S. Cl.
    CPC ........ *B01D 21/307* (2013.01); *B01D 2221/10* (2013.01); *B01L 2200/0689* (2013.01); *B01L 2400/0409* (2013.01); *G01N 33/491* (2013.01)

(56) References Cited

U.S. PATENT DOCUMENTS

| | | | |
|---|---|---|---|
| 4,843,869 A | 7/1989 | Levine et al. | |
| 5,269,927 A * | 12/1993 | Fiehler | B01L 3/50215 210/513 |
| 5,632,905 A * | 5/1997 | Haynes | B01L 3/50215 210/782 |
| 6,280,400 B1 | 8/2001 | Niermann | |
| 6,406,671 B1 * | 6/2002 | DiCesare | B01L 3/50215 210/512.1 |
| 6,409,528 B1 | 6/2002 | Bodnar | |
| 6,479,298 B1 * | 11/2002 | Miller | B01L 3/50215 210/121 |
| 6,537,503 B1 * | 3/2003 | Conway | B01L 3/50215 210/789 |
| 7,188,734 B2 * | 3/2007 | Konrad | B01L 3/5021 210/513 |
| 8,998,000 B2 * | 4/2015 | Crawford | B01D 17/0217 210/512.1 |
| 9,333,455 B2 * | 5/2016 | Gil | B01D 53/1493 |
| 9,364,828 B2 * | 6/2016 | Crawford | B01L 3/50215 |
| 9,731,290 B2 * | 8/2017 | Crawford | B01D 17/0217 |
| 9,919,307 B2 * | 3/2018 | Crawford | B01L 3/50215 |
| 10,376,879 B2 * | 8/2019 | Crawford | B01L 3/50215 |
| 10,456,782 B2 * | 10/2019 | Crawford | G01N 1/34 |
| 10,807,088 B2 * | 10/2020 | Crawford | G01N 1/34 |
| 2002/0094305 A1 | 7/2002 | DiCesare et al. | |
| 2002/0132367 A1 | 9/2002 | Miller et al. | |
| 2002/0156439 A1 * | 10/2002 | Iskra | B01L 3/5082 604/317 |
| 2005/0059163 A1 * | 3/2005 | Dastane | A61B 5/150351 436/177 |
| 2011/0036786 A1 * | 2/2011 | Ellsworth | B01D 21/262 210/789 |
| 2013/0315798 A1 | 11/2013 | Crawford et al. | |
| 2016/0136640 A1 | 5/2016 | Losada et al. | |

FOREIGN PATENT DOCUMENTS

| | | |
|---|---|---|
| EP | 0017127 A2 | 10/1980 |
| EP | 0098150 A2 | 1/1984 |
| EP | 0753741 A1 | 1/1997 |
| EP | 1106252 A2 | 6/2001 |
| JP | H09222427 A | 8/1997 |
| WO | 2009073232 A1 | 6/2009 |
| WO | 2010132783 A1 | 11/2010 |
| WO | 2014120678 A2 | 8/2014 |
| WO | 2016076911 A1 | 5/2016 |

\* cited by examiner

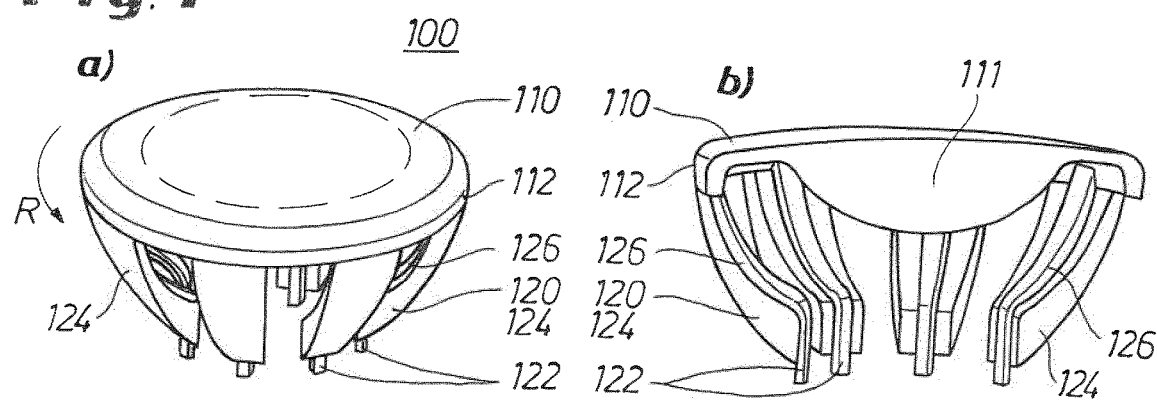
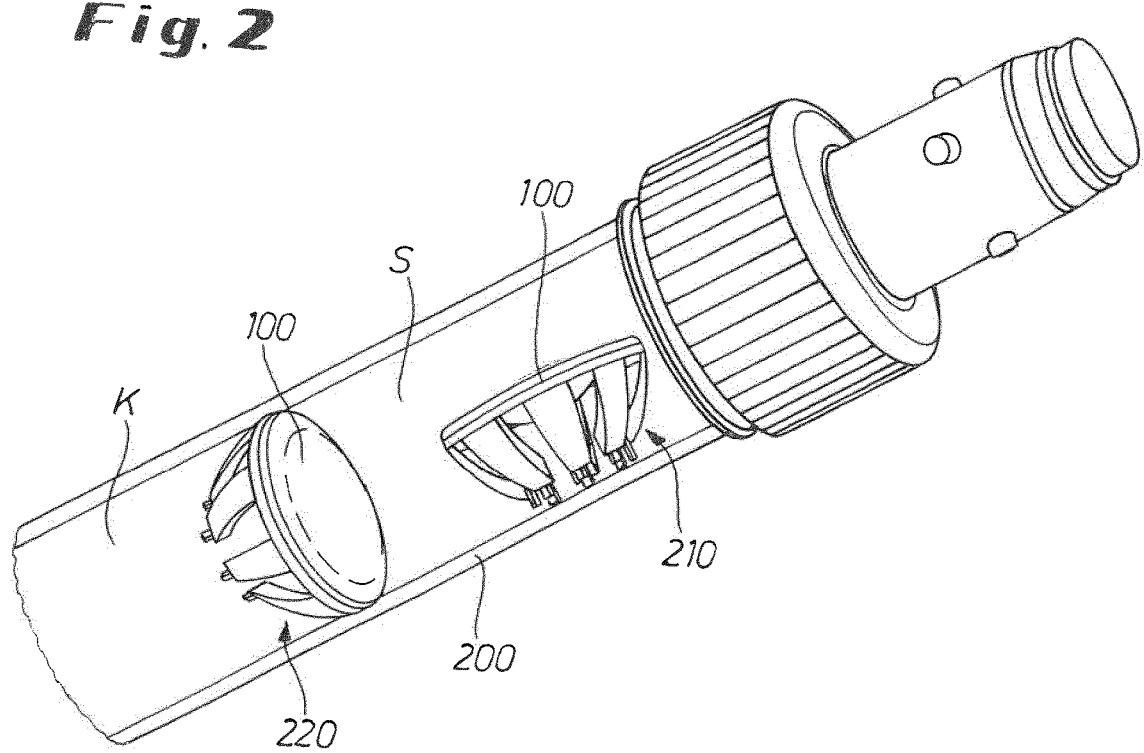

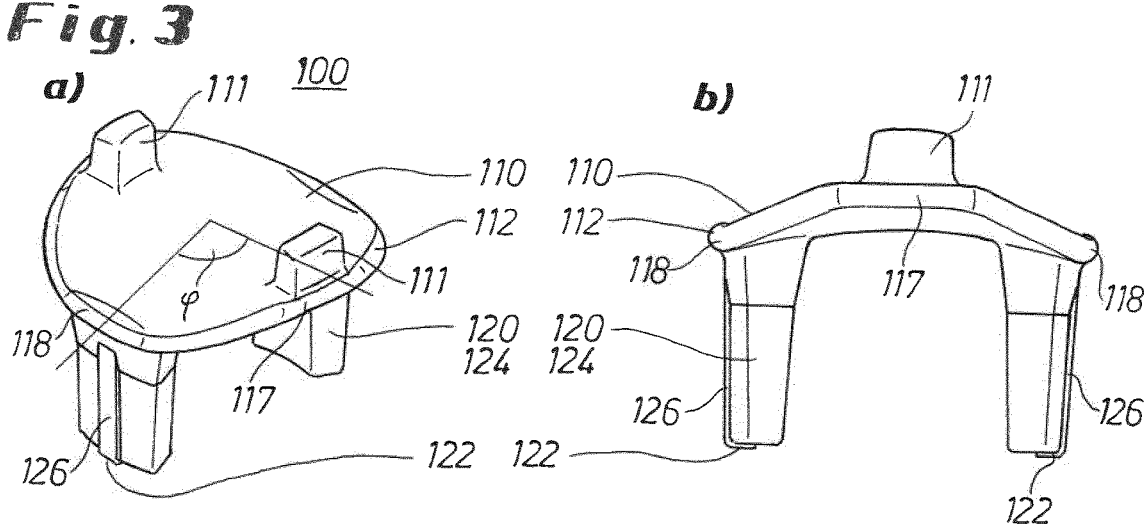
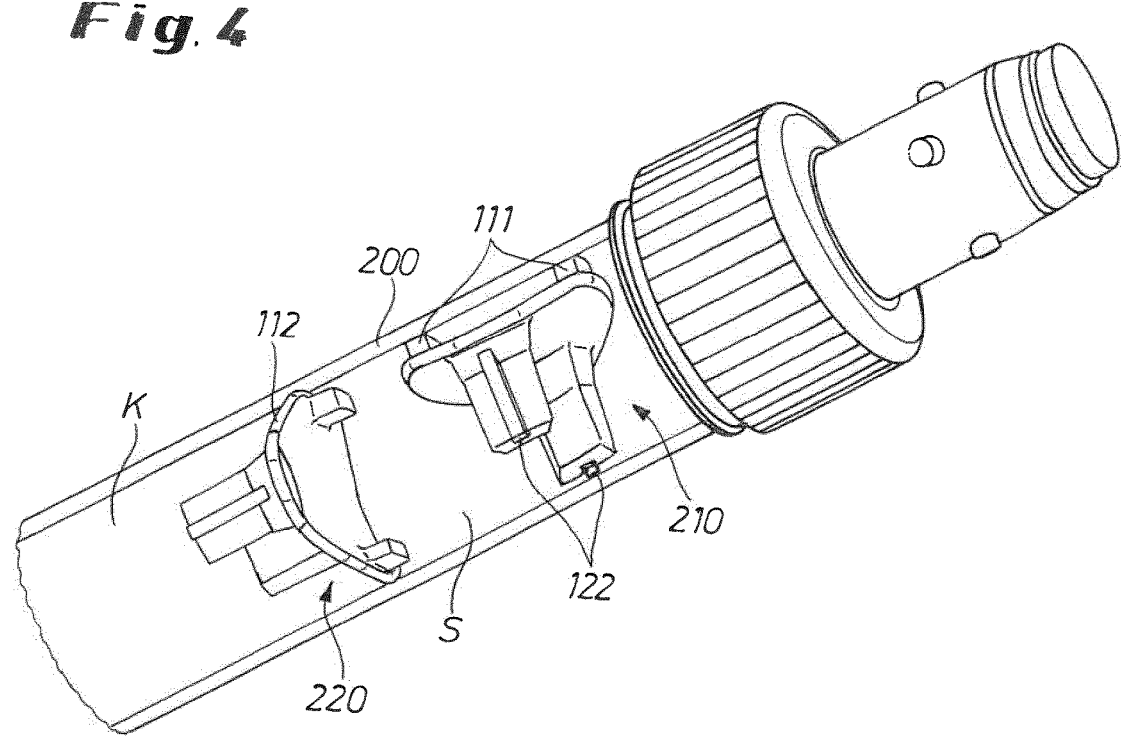

SEPARATOR

TECHNICAL FIELD

The invention relates to a separator for separating a first from a second phase of a liquid in a tubular container. In particular, separators are meant to separate blood serum being the first phase from cruor being the second phase in blood being the liquid within a blood collection tube.

BACKGROUND

Blood collection tubes having separators are generally known in the prior art. In a delivery state the separators are fixed in an initial position of the blood collection tubes. When blood flows into the blood collection tube via an inlet, it flows around or through the separator; in any case, in the initial position, the separator does not constitute a seal for the blood within the blood collection tube. For medical analysis it is necessary for the blood to be separated into two components, namely blood serum and cruor. For this purpose, the blood collection tube with the blood located therein is centrifuged. The heavier cruor then settles due to centrifugation in the volume region near the bottom of the blood collection tube, while the lighter blood serum floats on the cruor. The separator detaches from its initial position and moves into a sealing position under the action of the centrifugal force. Because the density of the entire separator lies in a value range between the density of the blood serum and the density of the cruor, the separator automatically positions itself exactly at the phase boundary between blood serum and cruor. This position is also referred to as sealing position, because in this position, the separator rests with its sealing edge circumferentially against the inner side of the tubular sample tube in a sealing manner and thus separates the blood serum from the cruor. The separator maintains this sealing position even after the end of centrifugation so that the blood serum and the cruor are separately available for a laboratory examination.

Separators are disclosed, for example, in international patent application WO 2010/132783 A1. The separators described therein each have a float made of elastic material having a sealing edge that is circularly circumferential in top view, wherein, in a sealing position, the sealing edge is designed for resting against the inner side of a tubular sample container in a sealing manner. A ballast is fastened in each case to the underside of the float. The density of the ballast is in each case greater than the density of the float and the density of the entire separator lies in a value range between the density of the first phase and the density of the second phase of the liquid.

The prior art in the form of document WO 2016/076911 A1 discloses a separation unit for separating a liquid into a first light phase and a second heavier phase using centrifugal force, wherein the liquid can be blood. A tubular container has a separator, wherein the separator has a float in the upper region and a ballast in the lower region. The separator is designed for resting against the inner side of the tubular container in a sealing manner. The density of the ballast in this case is greater than the density of the float and the density of the separator lies between the density of the first phase and the density of the second phase of the liquid to be separated.

Document DE 699 31 584 T2 describes a device for separating a fluid sample under centrifugal force into a phase having a higher specific gravity and a phase having a lower specific gravity, wherein the fluid sample can be a blood sample. The device has a separator element (separator) which is arranged in a cylindrical tube. The separator element has a float in the upper region and a ballast element in the lower region and a sealing body resting against the inner side of the tube in a sealing manner. The density of the ballast in this case is greater than the density of the float and the entire density of the separator lies between the density of the first phase and the density of the second phase of the liquid to be separated.

Document DE 600 23 823 T2 includes a device for separating a liquid sample (for example, blood) into a first phase of high density and into a phase of low density under the action of centrifugal force. A separator is arranged in a tube having a cylindrical side wall, which separator has a float in the upper region and a ballast part in the lower region and a bellows for resting against the inner side of the tube in a sealing manner. The density of the ballast part in this case is greater than the density of the float and the entire density of the separator lies between the densities of the first phase and the second phase of the liquid to be separated.

Document U.S. Pat. No. 5,632,905 A relates to the separation of a blood sample into a lighter and a heavier phase by centrifuging in a tube. A separator is arranged in the tube. The separator has a disk-like shape and rests in a sealing position against the phase boundary between lighter and heavier phase.

SUMMARY

The invention has for its object to provide an alternative separator for separating a first from a second phase of a liquid in a tubular container.

This object is achieved with regard to the separator by the subject matter as claimed. The separator is characterized in that the float is designed disk-shaped and that the ballast is designed in the shape of a plurality of fingers, which extend away from the underside of the disk-shaped float, distributed at its edge.

In the delivery state, respectively in its initial position, the separator is detachably clamped in the tubular container. In this delivery state the separator is arranged transverse in the container. There, the ballast pushes with ends of its fingers facing away from the float against the inner side of the tubular container. In other words, the separator is supported in this initial position against the tubular container as described.

The open design of the separator and in particular its ballast in the form of fingers advantageously ensures that the separator does not seal the tubular container in its initial position in the delivery state for the liquid, but that liquid flowing into the container can flow around the separator, so in that the liquid can flow into volume regions of the tubular container located below the separator.

Under the action of a force, in particular a centrifugal force, the separator detaches from this initial position and moves into the sealing position within the tubular container. The preferably uniform distribution of the fingers of the ballast body on the circumference of the float advantageously causes the separator to become evenly thinner under the action of the force, distributed over its circumference, that is, its diameter is reduced uniformly over its circumference. As a result, said movement of the separator is supported in that it cannot get stuck on the inner side of the container when it is moving.

In general: The density of the second phase of the liquid is greater than the density of the first phase of the liquid. For blood as a liquid, this means that the cruor as the second phase has a greater density than the blood serum, which corresponds to the first phase. The blood serum therefore floats on the cruor after a centrifugation. The density of the entire separator lies in a value range between the density of the first phase and the density of the second phase of the liquid. Therefore, the separator always positions itself in the sealing position on the phase boundary between the two phases.

Unless otherwise stated, the separator is described in the following in a normal position. The ballast is arranged below the float in this normal position. The center of gravity of the float, the center of gravity of the ballast and the center of gravity of the entire separator all lie on a vertical line. The terms used in the following, such as vertical, horizontal, below, side view and top view, etc., all refer to this normal position. The sealing position corresponds to the normal position where the tubular container is vertical.

According to a first embodiment, the disk-shaped float has a bulges in its center. This bulges serves as a buoyancy body and ensures that the separator floats on the heavier second phase of the liquid within the tubular container.

Alternatively or in addition to the central bulges, the disk-shaped float can also have buoyancy bodies distributed on its edge. Preferably, these buoyancy bodies are arranged in the circumferential direction alternatingly with the fingers. Further alternatively, the buoyancy bodies can be arranged rising on the upper side of the disk-shaped float, while the fingers, as stated, extend downwardly from the underside of the disk-shaped float. When the buoyancy bodies and the fingers extend in respectively opposite directions, this has the advantage that the centers of gravity of the float and the ballast have a large distance from one another. This is advantageous to obtain a stable position of the separator at the phase boundary and thus a secure separation of the two phases of the liquid within the tubular container.

When the disk-shaped float is not spherically deformed, its side edge extends, viewed in a side view, straight, preferably horizontal. Alternatively, the disk-shaped float can also be spherically deformed. In the side view, its sealing edge then extends wave-shaped with wave crests and wave troughs. Preferably, the fingers of the ballast are then respectively arranged in the region of the wave troughs and the bulges or buoyancy bodies in the regions of the wave crests on the edge of the float. This particular embodiment of the separator advantageously favors a thinning of the separator when it moves, under the action of the centrifugal force, from its initial position into the sealing position.

Finally, at least some of the fingers can have an adhesive element at their free ends, which adhesive element is characterized by a predetermined static friction coefficient on its surface.

The adhesive element can be formed from the same material as the float and preferably in one piece with the float. The adhesive element is then advantageously inexpensive to manufacture and easy to realize. The one-piece design with the float can be realized, for example, simply by providing small channels in an injection mold for the separator on the outer side or in the interior of the ballast body, which channels connect the float to the adhesive element. During injection molding of the float, the material of the float is then injected through the channels into the cavities for the adhesive elements. After removal of the injection mold, the material of the float remains in the region of the channels of the injection mold on the outer side or in the interior of the ballast body in the form of webs, which connect the float to the adhesive element in one piece. The webs are only optional. The float and the adhesive elements can also be designed independently of each other as individual elements, but this is more complex to manufacture.

Further advantageous embodiments of the separator are the subject of the dependent claims.

BRIEF DESCRIPTION OF THE DRAWINGS

FIGS. 1a and 1b show a separator having disk-shaped float according to a first variant.

FIG. 2 shows the separator according to FIGS. 1a and 1b in a tubular container.

FIGS. 3a and 3b show a disk-shaped separator according to a second variant.

FIG. 4 shows the separator according to FIGS. 3a and 3b in a tubular container.

DETAILED DESCRIPTION

The invention is described in detail in the following with reference to said figures in the form of exemplary embodiments. The same technical elements are designated by the same reference numerals in all figures.

FIGS. 1a and 1b shows the separator 100 in a perspective view (FIG. 1a) and in a cross-sectional representation (FIG. 1b). The separator 100 consists of a float 110 and a ballast 120. The float 110 is designed disk-shaped having a bulge 113 in its center and having a circumferential sealing edge 112. The ballast body 120 is designed in the form of a plurality of fingers 124 which extend away from the underside of the disk-shaped float 110. The fingers 124 are arranged distributed on the edge of the ballast body. The fingers preferably each have adhesive elements 122 at their ends facing away from the float, which adhesive elements have a predetermined static friction coefficient on their surface. In this way, it is ensured that the separator remains in its initial position or its delivery state within the tubular container until it experiences a force which is greater than a predetermined force threshold value.

The adhesive element 122 is designed in the embodiment shown in FIGS. 1a and 1b of the same material as the float 110 and even as one piece therewith. This can be seen in FIG. 1b in that the material of the float 110 is designed on the outer side of the ballast 120 in the form of webs 126, which connect the float in one piece to the adhesive element 122.

FIG. 2 shows the separator 100 in the tubular container 200, for example, a blood collection tube. The separator 100 can be seen, on the one hand, in its initial position 210, in which it is located when the tubular container 200 is delivered. In this initial position, the separator is supported by said adhesive elements 122 on the inner side of the tubular container. The separator 100 is detached from its initial position 210 and moves into a sealing position 220 only under the action of the centrifugal force. At the same time, it turns by 90°. The separator 100 deforms back into its starting state only when it is no longer under the action of the centrifugal force. Its sealing edge 112, in the sealing position 220 in the circumferential direction R, rests everywhere against the inner side of the tubular container 200 in a sealing manner and in this way, separates the two phases of the liquid or the blood effectively from each other.

FIGS. 3a and 3b shows the separator 100 in an alternative configuration. FIG. 3a shows it in a perspective view, and FIG. 3b shows it in a side view. Here, the float 110 is also formed generally disk-shaped, but it is spherically deformed. Therefore, the circumferential edge 112 is formed wave-shaped with wave troughs 118 and wave crests 117 when viewed from the side. Ballast bodies 120 stick out in the shape of fingers 124 downward from the underside of the disk-shaped float 110 in each case in the region of the wave troughs 118. Preferably, each of these fingers has said adhesive element 122 at its end facing away from the float 110. Material accumulations on the upper side of the disk-shaped float are designed in the region of the wave crests 117. These accumulations act as additional buoyancy bodies 111. In the embodiment shown in FIG. 3a, the fingers 124 and the buoyancy bodies 113 are respectively arranged alternately distributed at a circumferential angular distance of φ=90° at the periphery of the disk-shaped float.

This special arrangement of buoyancy bodies and ballast bodies is particularly advantageous for the movement of the separator from the initial position into the sealing position. The force acting on the separator, in particular the centrifugal force, causes the float 110 to become even more spherically deformed relative to its initial shape. This is because the lifting of the buoyancy bodies 111 pulls the wave crests 117 further upwards and because at the same time, the fingers 124 of the ballast in the region of the wave troughs 118 are pulled further downwards. Due to this even stronger spherical deformation, the separator 100 becomes thinner and the sealing edge 112 of the float no longer rests against the inner side of the tubular container in a sealing manner. The liquid or the blood can therefore, as desired, flow around the float as the float moves into the sealing position 220.

FIG. 4 shows the separator according to FIGS. 3a and 3b in the interior of the tubular container 200. In the delivery state the separator is located in its initial position 210. It is there propped up on the one side with the free ends of the fingers, possibly with the adhesive elements 122 located thereon, and on the other side, with the free ends of the buoyancy bodies 111 against the inner side of the tubular container 200. The free ends of the buoyancy bodies 111 are therefore preferably rounded in accordance with the inner radius of the tubular container 200. In the initial position 210, blood flowing into the tubular container can flow around the separator 100, as described above, in particular based on its open design so that the blood can reach deeper volume regions of the tubular container.

With regard to the behavior of the separator 100 under the action of the centrifugal force and upon removal of the centrifugal force, reference is made to the description of FIG. 2, which applies analogously to FIG. 4.

LIST OF REFERENCE NUMERALS 100 separator
110 float
111 bulge/buoyancy body
112 sealing edge
117 wave crest of the sealing edge
118 wave trough of the sealing edge
120 ballast
122 adhesive element
124 fingers
126 webs
200 container
210 initial position
220 sealing position
K cruor
S blood serum
φ circumferential angular distance
R circumferential direction

The invention claimed is:

1. A separator (100) for separating a first phase from a second phase of a liquid under centrifugal force in a tubular container (200), comprising:
   a float (110) made of elastic material having a circumferential sealing edge (112) which rests against an inner side of the tubular container (200) in a sealing manner when the separator is in a sealing position (220); and
   at least one ballast (120) fastened to an underside of the float (110)
   wherein a density of a material of the ballast (120) is greater than a density of a material of the float (110),
   wherein a density of the separator (100) lies in a value range between a density of the first phase and a density of the second phase of the liquid,
   wherein the float (110) is disk-shaped,
   wherein the ballast (120) is in a shape of a plurality of fingers (124) which extend away from an underside of the disk-shaped float (110), distributed along its edge, and
   wherein the disk-shaped float (110) has bulges as buoyancy bodies (111) distributed along its edge arranged alternately with the fingers.

2. The separator (100) according to claim 1, wherein the liquid is blood, the first phase is blood serum and the second phase is cruor.

3. The separator (100) according to claim 1, wherein the disk-shaped float (110) has a bulge in its center as a buoyancy body (111).

4. The separator (100) according to claim 1, wherein the buoyancy bodies (111) and the fingers (124) are arranged on opposite sides of the disk-shaped float (110).

5. The separator (100) according to claim 1, wherein the fingers (124) and the buoyancy bodies (111) are arranged distributed at an equal circumferential angular distance (φ) alternately at the edge of the float (110).

6. The separator (100) according to claim 5,
   wherein two buoyancy bodies (111) and two fingers (124) are arranged at the edge of the float, and
   wherein there is each an angular distance (φ) of 90° between one of the buoyancy bodies and one of the fingers (124).

7. The separator (100) according to claim 1, wherein the sealing edge (112) extends straight.

8. The separator (100) according to claim 1, wherein the sealing edge (112) extends horizontally.

9. The separator (100) according to claim 1,
   wherein the disk-shaped float (110) is spherically deformed having a wave-shaped sealing edge (112) with wave crests (117) and wave troughs (118), and
   wherein the fingers (124) of the ballast (120) are arranged in a region of the wave troughs (118) and the bulges (111) of the float (110) in a region of the wave crests (117) on the edge of the float (110).

10. The separator (100) according to claim 1,
    wherein at least one of the fingers (124) has an adhesive element (122) arranged at a free end facing away from the float (110), the adhesive element having a predetermined static friction coefficient on its surface.

11. The separator (100) according to claim 10, wherein the adhesive element (122) is made of the same material as the float.

12. The separator (100) according to claim 11, wherein the adhesive element (122) and the float are one piece.

* * * * *